(12) United States Patent
Prasad et al.

(10) Patent No.: US 6,656,420 B2
(45) Date of Patent: Dec. 2, 2003

(54) DENTAL ALLOYS

(75) Inventors: Arun Prasad, Cheshire, CT (US); Martin L. Schulman, Orange, CT (US); Grant P. Day, Cheshire, CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/770,786

(22) Filed: Jan. 26, 2001

(65) Prior Publication Data

US 2002/0004018 A1 Jan. 10, 2002

Related U.S. Application Data

(60) Provisional application No. 60/178,173, filed on Jan. 26, 2000.

(51) Int. Cl.$^7$ .......................... C22C 5/02; C22C 30/00
(52) U.S. Cl. ................ 420/512; 148/430; 148/442; 420/580
(58) Field of Search .................. 420/507, 508, 420/509, 510, 511, 512, 580; 148/430, 442

(56) References Cited

U.S. PATENT DOCUMENTS

| | | | |
|---|---|---|---|
| 2,506,526 A | 5/1950 | Tifft | |
| 4,062,676 A | 12/1977 | Knosp | |
| 4,539,177 A | 9/1985 | Prasad | |
| RE32,005 E | * 10/1985 | Miyazaki | ................ 148/31.55 |
| 4,576,789 A | 3/1986 | Prasad | |
| 4,661,071 A | 4/1987 | Bell et al. | |
| 4,828,495 A | 5/1989 | Bell et al. | |
| 5,091,148 A | 2/1992 | Prasad | |
| 5,423,680 A | * 6/1995 | Prasad | ........................ 433/207 |
| 5,462,437 A | 10/1995 | Prasad et al. | |

FOREIGN PATENT DOCUMENTS

| | | | |
|---|---|---|---|
| DE | 684186 | 12/1939 | |
| DE | 2424575 | 12/1975 | |
| JP | 52-135823 A | * 11/1977 | ............. C22C/5/02 |
| JP | 55-047346 | 3/1980 | |
| JP | 55-047360 | 3/1980 | |
| JP | 55-047353 A | * 4/1980 | ........... C22C/19/07 |

OTHER PUBLICATIONS

Abstrat of SE 8002785 A, Fredriksso et al, published Nov. 16, 1981.*

* cited by examiner

*Primary Examiner*—Roy King
*Assistant Examiner*—Harry D. Wilkins
(74) *Attorney, Agent, or Firm*—Ann M. Knab

(57) ABSTRACT

Dental alloys are provided having a coefficient of thermal expansion in the range from about 8 to about $18 \times 10^{-6}/°$ C. in the temperature range of 25–500° C. and melting temperatures above about 800° C. but below about 1500° C. The alloys contain gold in combination with a small amount of chromium and/or tantalum. Other elements may also be included with the gold and chromium and/or tantalum to provide the necessary forming, melting, and mechanical properties required to manufacture the desired dental restoration.

12 Claims, No Drawings

DENTAL ALLOYS

CROSS-REFERENCE TO RELATED APPLICATIONS

This is application claims priority to U.S. Provisional Application No. 60/178,173 filed Jan. 26, 2000, which is incorporated herein by reference.

FIELD OF THE INVENTION

This invention relates to gold-based dental alloys for use in dental restorations.

BACKGROUND OF THE INVENTION

Gold-based alloys in dentistry were initially replaced by more economical palladium-based alloys. Recent increases in the price of palladium are making these alloys very expensive. Other economical alternatives have been nickel-based, cobalt-based and titanium-based systems. Nickel-based alloys allegedly have sensitivity concerns for some people. Cobalt-based and titanium-based alloys are difficult to process and require special care and expensive equipment.

Prior solutions to the problem have been to use metal-free ceramic/composite systems or sintered or plated copings. It is desirable to provide alloys for use in the manufacture of dental restorations having little or no palladium therein. It is further desirable that the alloys have high strength and are easily formable into dental restorations.

SUMMARY OF THE INVENTION

These and other objects and advantages are accomplished by the alloys herein having a coefficient of thermal expansion in the range from about 8 to about $18 \times 10^{-6}/°$ C. in the temperature range of 25–500° C. and melting temperatures above about 800° C. but below about 1500° C. The alloys herein contain gold in combination with a small amount of chromium and/or tantalum. Other elements may also be included with the gold and chromium and/or tantalum to provide the necessary forming, melting, mechanical and similar properties required to manufacture the desired dental restoration. The alloys are particularly useful as substrate components for dental restorative materials including, but not limited to, orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors. The substrate may be defined as a main component of the dental restoration having one or more layers of material thereon, or as the complete restoration with no other material thereon.

DESCRIPTION OF THE INVENTION

The dental alloys herein are formulated to have a coefficient of thermal expansion which is in the range from about 8 to about $18 \times 10^{-6}/°$ C. in the temperature range of 25–500° C. Melting temperatures must be above about 800° C. but below about 1500° C. The most preferred melting range is from about 1000° to about 1350° C. The alloys are particularly well suited for being coated with a wide variety of composites and porcelain compositions.

The alloys herein contain gold in combination with a small amount of chromium and/or tantalum. Chromium and tantalum are useful for a variety of reasons. They tend to improve corrosion resistance, lower melting temperature and strengthen the alloy. Other elements may also be included with the gold and chromium and/or tantalum. The ranges of the alloy compositions are contained in Table 1 below.

TABLE 1

| Elements | Range 1 (wt %) | Range 2 (wt %) | Range 3 (wt %) | Range 4 (wt %) |
| --- | --- | --- | --- | --- |
| Au | 15–85% | 20–70 | 25–60 | 30–50 |
| Co/Fe, singly or in combination | 0–65 | 0–60 | 10–50 | 20–30 |
| Cr/Ta, singly or in combination | 1–30 | 2–25 | 5–20 | 10–15 |
| Nb/Mo/W/V singly or in combination | 0–15 | 0–15 | 0–10 | 0–8 |
| In,Ga,Sn,Ge, singly or in combination | 0–10 | 0–10 | 0–5 | 0–5 |
| Ni,Pd,Pt,Cu,Mn, singly or in combination | 0–30 | 0–30 | 5–30 | 10–20 |
| Ir,Ru,Re,Ti,Al,Si,Hf, singly or in combination | 0–5 | 0–5 | 0–3 | 0–2 |
| Zr,B,Y, and rare earths, singly or in combination | 0–5 | 0–5 | 0–1 | 0–1 |

The preferred alloys of this invention fall under the noble or the high noble categories of the American Dental Association (ADA). According to the ADA classification, the high noble category requires the noble metal content to be greater than 60% and requires the gold content to be greater than 40%. The noble category requires the noble metal content to be equal to or greater than 25%. The preferred properties of the alloys herein must possess properties better than the alloys as per ISO 9693.

The selection of an element or combination of elements in Table 1 above may be dependent on the thermal expansion coefficient of the overlay material. The thermal expansion of the alloy is adjusted to be slightly greater than the thermal expansion of the overlay material. Matching the thermal expansions in this manner enables the formation of compressive stress at the interface between the alloy and the overlay material. Achieving this condition strengthens the overlay material which is generally weaker than the alloy substrate.

It may be desirable to alter the coefficient of thermal expansion depending upon the use of the alloy. This can be done by the addition of certain elements. The elements that lower the melting point will have a tendency to raise the coefficient of thermal expansion. Such elements include, but are not limited to, indium, gallium, tantalum, cobalt, nickel and tin. Elements that raise the melting point will have a tendency to lower the coefficient of thermal expansion. Such elements include, but are not limited to, platinum, palladium, iron, tungsten and molybdenum.

Ruthenium or rhenium may serve as grain refining agents in the alloys. Grain refiners are sometimes added to the alloy to control grain size by providing stable embryos as the alloy melt solidifies. The smaller the grain size, the better the formability of the alloy and the greater the number of grains over the thickness of the alloy. Smaller grain sizes also make the alloy less vulnerable to heat tears or cracks during casting of thin wall copings. Smaller grain size in an alloy additionally enables the edges and margins of the casting to be non-ragged and easily burnished. A margin is defined herein as the area where the dental coping comes in contact with gum tissue.

The following Table 2 sets forth examples of alloys prepared for use as dental restorative materials. The alloys herein are particularly useful as substrate components for dental restorative materials including, but not limited to, orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors. The substrate may be defined as a main component of the dental restoration having one or more layers of material thereon, or as the complete restoration with no other material thereon.

cured by means such as photo-initiation; chemical curing; heat curing; combinations of photo-initiation and chemical curing; and combinations of photo-initiation chemical curing and heat curing. The curing may also be conducted under water, under vacuum and under pressure of inert gases. One such composite is Sculpture® composite available from Jeneric/Pentron Inc.

TABLE 2

|  | 1 | 2 | 3 | 4 | 5 | 6 | 7 | 8 |
|---|---|---|---|---|---|---|---|---|
| Au | 50.00 | 50.00 | 40.00 | 60.00 | 60.00 | 40.00 | 72 | 32.55 |
| Pd | 25.00 | 25.00 | 0.00 | 0.00 | 0.00 | 0.00 | 0 | 30 |
| Pt | 0.00 | 0.00 | 0.00 | 0.00 | 0.00 | 0.00 | 0 | 1 |
| Co | 25.00 | 0.00 | 33.60 | 28.00 | 0.00 | 42.00 | 0 | 30 |
| Fe | 0.00 | 25.00 | 0.00 | 0.00 | 28.00 | 0.00 | 0 | 0 |
| Cr | 0.00 | 0.00 | 12.12 | 12.00 | 12.00 | 18.00 | 6 | 5 |
| Ta | 0.00 | 0.00 | 12.00 | 0.00 | 0.00 | 0.00 | 0 | 0 |
| Ni | 0.00 | 0.00 | 0.00 | 0.00 | 0.00 | 0.00 | 22 | 0 |
| Al | 0.00 | 0.00 | 1.80 | 0.00 | 0.00 | 0.00 | 0 | 1.25 |
| Y | 0.00 | 0.00 | 0.00 | 0.00 | 0.00 | 0.00 | 0 | 0.1 |
| Mn | 0.00 | 0.00 | 0.30 | 0.00 | 0.00 | 0.00 | 0 | 0 |
| Hf | 0.00 | 0.00 | 0.18 | 0.00 | 0.00 | 0.00 | 0 | 0 |
| Ir | 0.00 | 0.00 | 0.00 | 0.00 | 0.00 | 0.00 | 0 | 0.1 |
| Total | 100.00 | 100.00 | 100.00 | 100.00 | 100.00 | 100.00 | 100 | 100 |
| CTE | 14.86 | 15.57 | 16.61 | 16.05 | 13.84 | 15.84 | 14.95 | 13.6 |
|  | 14.80 | 15.74 | 17.36 | 15.96 | 14.22 | 15.89 | 15.2 | 13.9 |
| Solidus ° C. | 1058.00 | 1219.00 | — | 1073.00 | — | 1089.00 | 975 | 1150 |
| Liquidus ° C. | 1136.00 | 1239.00 | — | 1330.00 | — | 1331.00 | 1000 | 1180 |

Generally, the gold and chromium and/or tantalun are melted together under a protective (oxygen deficient) atmosphere, optionally in the presence of other metals as set forth in the tables above. The metals are alloyed using standard melting techniques. To incorporate certain elements into the alloys, master alloys may be used in combination with single metals. These master alloys include, but are not limited to Au—Ta (12% Ta), Co—Ta (32.4% Ta) and Co—Cr (30% Cr). They are useful for controlling the composition during melting. Induction furnaces utilizing ceramic crucibles such $ZrO_2$, $Al_2O_3$ or MgO, are preferred for alloying since induction promotes stirring during the melting operation. Carbon-containing crucibles are not recommended.

A wide variety of porcelain mixtures form desirable porcelain coatings when fused to dental alloys. Different mixtures are preferred for the different layers of the restoration. The restoration may comprise a bond layer, an opaque porcelain layer, a body layer and an incisal layer. Differences in the components used for each layer and differences in the amounts of the components enable the different layers to exhibit different optical and thermal properties.

A preferred porcelain will have a fusion range of about 725° to about 950° C. and a coefficient of thermal expansion in the range from about 10 to about $17 \times 10^{-6}/°$ C. in the temperature range of 25–500° C. The dental porcelain may comprise oxides including but not limited to Si, Al, K, Na, Li, Ca, Mg, Zr, Ti, Sn, Y, Ce and Eu. Some commercially available porcelain compositions useful herein include Synspar® porcelain and OPC® Lowwear™ porcelain, both available from Jeneric/Pentron Inc., Wallingford, Conn. and Finesse™ porcelain from Dentsply, York, Pa.

A wide variety of composites can also be used and include those made of glass fillers and resins such as BIS-GMA, TEGDMA, UDMA and PCDMA. The composites may be While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains.

Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A dental alloy for the manufacture of a dental substrate for a dental restoration comprising by weight:

about 25 to about 60% Au;

about 5 to about 20% of one of Cr, Ta, or a combination thereof about 10 to about 50% Co; and about 5 to about 30% of one of Ni, Pd, Cu or a combination thereof.

2. The dental alloy of claim 1 further comprising by weight:

up to about 10% of one of Nb, Mo, W, V or a combination thereof up to about 5% of one of In, Ga, Sn, Ge or a combination thereof up to about 3% of one of Ir, Ru, Re, Ti, Al, Si, Hf or a combination thereof; and up to about 1% of one of Zr, B, Y, a rare earth metal or a combination thereof.

3. The dental alloy of claim 1 wherein the dental restoration is selected from the group consisting of orthodontic appliances, bridges, space maintainers, tooth replacement appliances, splints, crowns, partial crowns, dentures, posts, teeth, jackets, inlays, onlays, facing, veneers, facets, implants, abutments, cylinders, connectors and a combination thereof.

4. The dental alloy of claim 1 comprising a coefficient of expansion in the range from about 8 to about $18 \times 10^{-6}/°$ C. in the temperature range of 25–5000° C.

5. The dental alloy of claim 1 comprising a melting temperature in the range from about 800° C. to about 1500° C.

6. The dental alloy of claim 1 wherein the dental substrate comprises one or more porcelain or composite materials thereon.

7. A dental alloy for the manufacture of a dental substrate for a dental restoration comprising:
- about 30 to about 50% Au;
- about 10 to about 15% of one of Cr, Ta, or a combination thereof;
- about 20 to about 30% Co; and
- about 10 to about 20% of one of Ni, Pd, Cu, Mn, or a combination thereof.

8. The dental alloy of claim 7 further comprising by weight:
- up to about 8% of one of Nb, Mo, W, V or a combination thereof;
- up to about 5% of one of In, Ga, Sn, Ge or a combination thereof;
- up to about 2% of one of Ir, Ru, Re, Ti, Al, Si, Hf or a combination thereof; and
- up to about 1% of one of Zr, B, Y, a rare earth metal or a combination thereof.

9. The dental alloy of claim 7 wherein the dental restoration is selected from the group consisting of orthodontic appliances, bridges, space maintainers, tooth replacement appliances, splints, crowns, partial crowns, dentures, posts, teeth, jackets, inlays, onlays, facing, veneers, facets, implants, abutments, cylinders, connectors and a combination thereof.

10. The dental alloy of claim 7 comprising a coefficient of expansion in the range from about 8 to about $18 \times 10^{-6}/°$ C. in the temperature range of 25–500° C.

11. The dental alloy of claim 7 comprising a melting temperature in the range from about 800° C. to about 1500° C.

12. The dental alloy of claim 7 wherein the dental substrate comprises one or more porcelain or composite materials thereon.

* * * * *

UNITED STATES PATENT AND TRADEMARK OFFICE
CERTIFICATE OF CORRECTION

PATENT NO.   : 6,656,420 B2                                                                Page 1 of 1
DATED         : December 2, 2003
INVENTOR(S)  : Arun Prasad, Martin L. Schulman and Grant P. Day It is certified that error appears in the above-identified patent and that said Letters Patent is hereby corrected as shown below:

<u>Column 5,</u>
Line 7, delete "5000°" and insert therefor -- 500° --

Signed and Sealed this

Tenth Day of February, 2004

JON W. DUDAS
*Acting Director of the United States Patent and Trademark Office*